United States Patent [19]

Annoni

[11] Patent Number: 4,589,846
[45] Date of Patent: May 20, 1986

[54] TOOTH TRANSILLUMINATING LIGHT HOLDER

[76] Inventor: Jerry D. Annoni, 450 Maple Ave., Vallejo, Calif. 94591

[21] Appl. No.: 427,850

[22] Filed: Sep. 29, 1982

[51] Int. Cl.$^4$ .............................................. A61B 1/24
[52] U.S. Cl. .................................................. 433/30
[58] Field of Search .......................... 433/29, 139, 229

[56] References Cited

U.S. PATENT DOCUMENTS 1,122,086  12/1914  Dunlop ................................ 433/29

FOREIGN PATENT DOCUMENTS 2505798  2/1975  Fed. Rep. of Germany ........ 433/29

Primary Examiner—Robert Peshock
Attorney, Agent, or Firm—Donald Feix

[57] ABSTRACT

The tooth transilluminating light holder secures a lighting device to a tooth so that its light emitting end is perpendicular to the buccal (cheek) and lingual (tongue) surfaces of the tooth to be viewed. The tooth transilluminating light holder is supported at the tooth by a dental dam clamp to which it is affixed. Light provided to the surface of a tooth causes it to transilluminate, giving ample light within a drilled out tooth to accomplish endodontic (root canal) procedures. High intensity light is conducted along fiberoptic lines. These lines are inserted into the tooth transilluminating light holder and adjusted in and out to obtain proper proximity to the tooth's surface. This provides the desired transillumination within the tooth being viewed.

2 Claims, 7 Drawing Figures

TOOTH TRANSILLUMINATING LIGHT HOLDER

BACKGROUND OF THE INVENTION

1. Field of the Invention

The present invention relates to a holding and adjusting device for small diameter light transilluminating fiberoptic, wire like conduits. The light emitting ends of these small diameter conduits are inserted into the passages of the light holder. The holder is fabricated of an elasticized material. This, combined with correct sizing and placement of these passageways through the holder, allows the inserted conduit to be placed at, or near the surface of the tooth, at or below the gum line. The elasticized holder material can provide pressure on the gum around a tooth to assist the fiberoptic light in reaching the surface of the tooth just at, or below, the gum line.

2. Description of the Prior Art

Devices for securing light emitting ends of fiberoptic conduits to the surfaces of teeth for the purpose of transilluminating a tooth, have not been developed. Current methods for providing light to teeth to be examined, or to have surgical procedures performed, ranged from lights which are hand held and those mounted on portable moving instruments, to overhead holding light devices which attempt to beam or reflect light into the tooth. Previously, in order to see inside a tooth which had been drilled out in preparation for endodontic (root canal) procedures, light was reflected off a dental mirror directly into the tooth's drilled out cavity. This light bounced off the inner surfaces of the tooth and back again to the dental mirror for viewing. U.S. Pat. No. 4,184,196 to A. Moret, issued Nov. 24, 1976, is similar to the aforementioned hand held, or mounted lights for diagnostically checking teeth. It does not disclose a specific holding device which would stay in contact with, and move with, the head and tooth to be examined and treated.

U.S. Pat. No. 4,266,535 to A. Moret issued Apr. 12, 1979 discloses another portable light for the fluorescent excitation of a fluorescible material which is applied to teeth. No method of holding light near to, or in contact with, a tooth is disclosed.

U.S. Pat. No. 3,930,149 to French issued May 28, 1974 discloses a variable intensity dental lamp. Intensity of light to the tooth is varied by internal means and not by the pushing in, or pulling out, of the light within the light holder as disclosed in this invention.

In general, no device was discovered, either made in conjunction with, or made separately, generally or specifically, for the purpose of holding a high intensity light against, or near, to a tooth to transilluminate it for the purpose of examining its interior, or illuminating it to conduct endodontic procedures.

SUMMARY OF THE INVENTION

Briefly the present invention comprises small rectangular like blocks about ⅛" to 3/16" thick, made of a rubberized material with a horizontal hole through it. These blocks, called a tooth transilluminating light holder are sized to fit under the spreader wing extensions of a dental dam clamp and are bonded to its surface. When the dental dam clamp is secured in position on a tooth, the light emitting ends of fiberoptic conduits are inserted into passageways of the light holder. Passageways are fabricated in a perpendicular orientation to the lateral surfaces of the tooth and are sized to securely hold the conduit. This light emitting conduit can be adjusted towards, or away from, the surface of the tooth to vary the intensity of light occuring within it. This adjustment at the tooth expedites and conserves hand movement during endodontic procedures and provides shadow free illumination of the interior of the tooth.

STATEMENT OF THE OBJECTS OF THE INVENTION

An object of the present invention is to provide a means of securing fiberoptic conducted light to a tooth utilizing another commonly required device, namely, a dental rubber dam clamp, or similar type clamp, as its support. Another object of the present invention is to provide a light holder which functions to move the gum away from the gum line to further expose the surface of the tooth to facilitate locating the light emitting fiberoptic conduit in its optimum postion which is often at, or below, the gum line in the direction of the jaw bone.

Another object of the present invention is to direct and maintain high intensity light to a tooth which has been filled with photo sensitive dental filling material in order to better cure it through transillumination.

Other objects, advantages and novel features of the present invention will become apparent from the following detailed description of the invention when considered in conjunction with the accompanying drawings herein:

DESCRIPTION OF THE PREFERRED EMBODIMENTS

Figure 1:
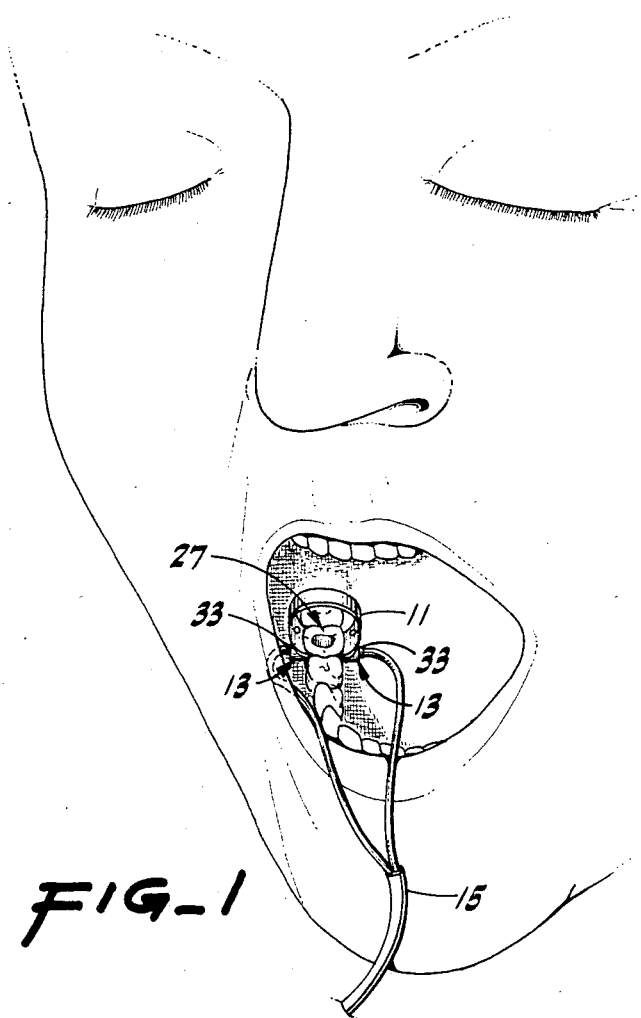
FIG. 1 is a perspective view showing the use of a tooth transilluminating light holder attached to a dental dam clamp with the fiberoptic light emitting ends of its conduit inserted in it as attached. (Dental dam rubber sheet is not shown).

In FIG. 1 are illustrated embodiments of the tooth transilluminating light holder. At the outset it should be noted that since the tooth transilluminating light holder, which will be referred to in this Preferred Embodiment section as the holder, is intended to be used primarily with a dental dam clamp and will be described and or implied as held by same. It is, however, understood that other similar, small, attaching or clamping devices are compatible with the intended function of this invention. Also, it is understood that the material, shape and firmness of the holder material may vary from elastic to unelastic plastic or metallic, and still remain compatible with the intent of this invention. Examples of this variation would be one or more stainless steel loops, or tubes, see FIG. No. 6 welded to the underside of the dental dam clamp, into which the light emitting end of the fiberoptic conduit could be inserted and held to, or against, the lateral surface of the tooth or several teeth to transilluminate single, or several, teeth, or a holder which is shaped flatter to accomodate ribbon type fiberoptics.

The holder 13 is kept in place in FIG. 1 by being bonded to clamp 11 and secures the fiberoptic conduit light emitting end 33. It should be understood that the fiber optic 15 can be replaced by light bulbs of small diameter powered by electric wires connected to it. Only the fiberoptic conduit referred to in the preferred embodiment section as conduit 15 and the light emitting sleeve ends 33 will be described herein.

Figure 2:
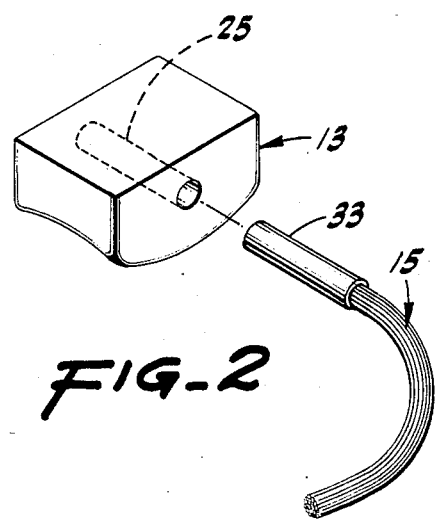
FIG. 2 is an enlarged isometric view of the tooth transilluminating light holder shown in FIG. 1.
Figure 3:
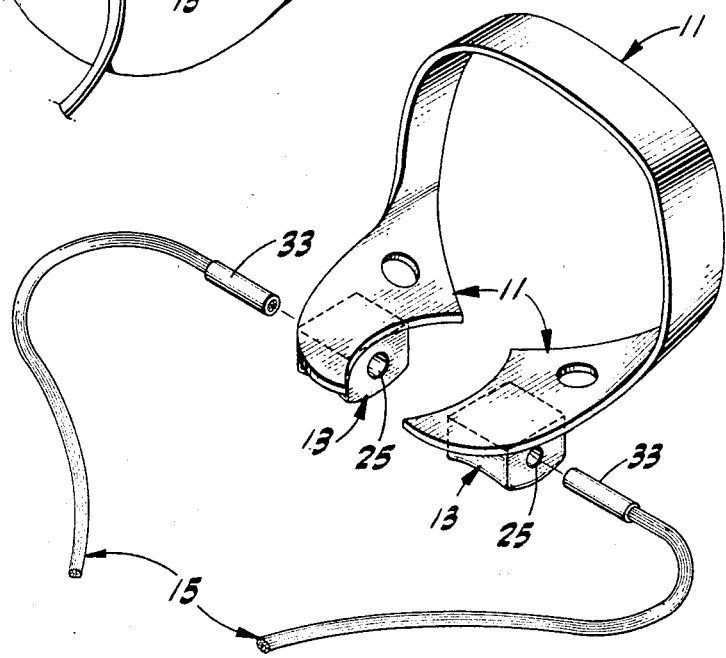
FIG. 3 is an enlarged isometric view of the tooth transilluminating light holder bonded to the dental dam clamp shown in FIG. 1.

In FIG. 2 we see one of the two rubberized holders 13 with its fiberoptic passage 25; into which the light emitting end 33 and its conduit 15 are inserted and held. The holder 13 is formed to fit the contour and be bonded to the dental dam clamp 11, as shown in FIG. 3.

Figure 4:
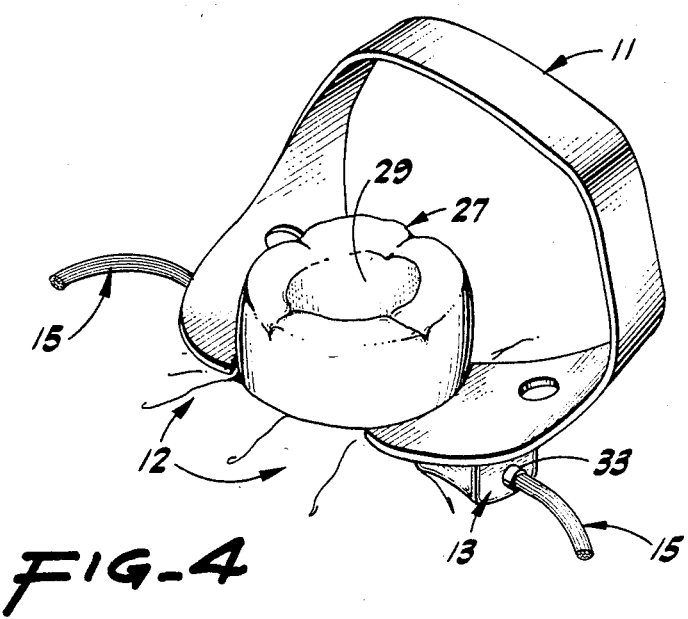
FIG. 4 is an enlarged isometric view of the tooth transilluminating light holder attached to the dental dam clamp with the fiberoptic conduits inserted in the holder as shown in FIG. 1 as it would appear with the tooth being transilluminated but removed from the mouth, in order to improve the clarity of detail in this document. A rubber dam covers the lower portion of the tooth.
Figure 6:
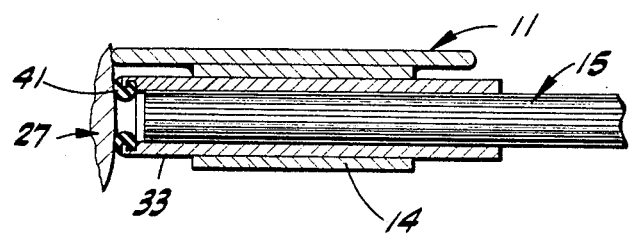
FIG. 6 is an enlarged view of a metallic type light holder with an O-ring tip. It functions in a similar manner to the elasticized holder; essentially fabricated of a stainless steel tube and welded to the underside of the wings of a dental rubber dam clamp. The said clamp holds the stainless steel tube which in turn holds the sleeved light emitting end of the fiberoptic conduit.

NOTE: Other methods of affixing the holder 13 to the dental clamp 11 are possible and meet fully the intent of this invention. The holder 13 can be fabricated with small protrusions which mate and affix it, in either a permanent or removable way, to mating holes fabricated in the dental dam clamp wings 11, as an example, of another embodiment. FIG. 4 shows the holder 13 in its use mode, as in FIG. 1, but completely exposed. The holder 13 is bonded to the dental dam clamp 11 which is shown clamped to the tooth 27. The light emitting ends 33 are inserted into the fiberoptic passage 25 (as shown in FIG. 2) where they can be adjusted in, or out, against, or near, the surface of the tooth 27. Note that the number of light emitting ends 33 need not be restricted to the two shown and that the location of the fiberoptic light passage holes 25 need not commence as shown but could commence from any side of holder 13 at any distance from said sides and at any angle required to bring the light to the tooth surface in a 90 degree angle, or any other angle, required for transilluminating the tooth 27 and thus fully meet the intention of the invention. The light emitting ends 33 and conduit 15 move towards, or away from, the surface of the tooth as adjusted by the user, while being held within the fiberoptic passage 25 (as shown in FIG. 5).

Figure 5:
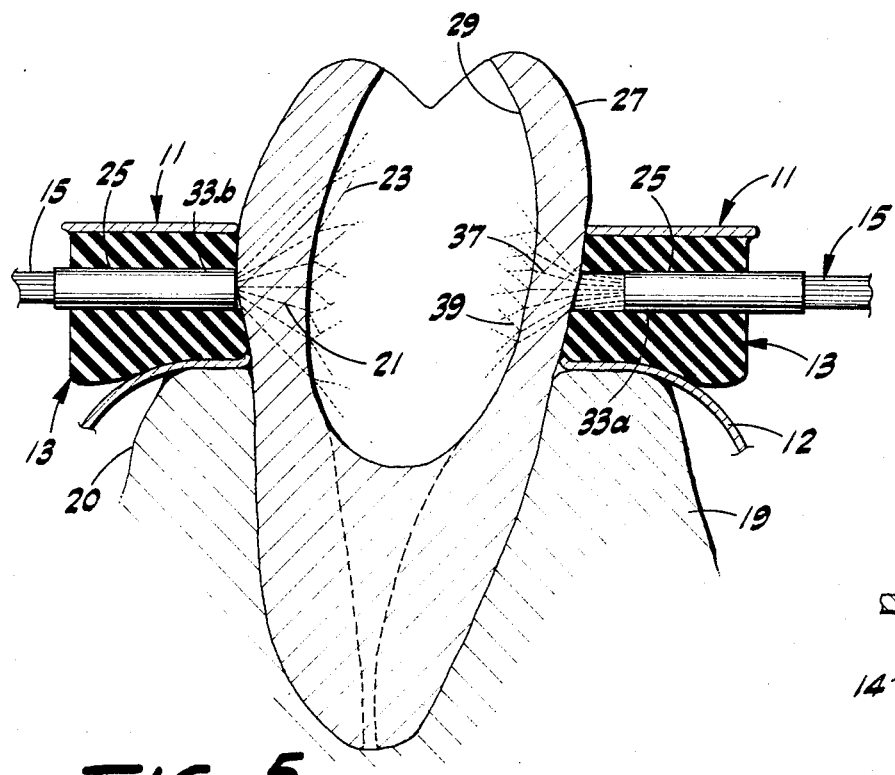
FIG. 5 is an enlarged cross section of the tooth and gum with the transilluminating light holder bonded to the dam clamp, fitted with the fiberoptic light conduits, transilluminating the tooth and being viewed from the position of an adjacent tooth. Here we see, on one side, the light emitting end of the conduit adjusted away from the tooth, and touching it on the other side. Also, we see the light holder gently, but effectively, depressing the gum to further expose the tooth surface. In so doing, the holder deforms as it presses down against the rubber dam and gum tissue.
Figure 7:
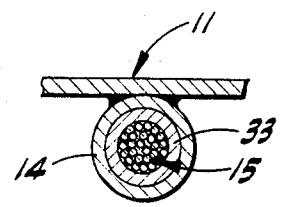
FIG. 7 is a cross section of FIG. 6.

FIG. 5 shows an enlarged cross sectional view of the holder 13, dental dam clamp 11, inserted fiberoptic light emitting ends 33a and 33b and conduits 15 all in position on tooth 27 as viewed from an adjacent tooth and looking back in the direction of the rear of the patient's head with the fully inserted light emitting end 33b in the holder 13, pressing against the surface of the tooth 27. The light emitting end 33a is slightly away from the surface of the tooth 27, though the holder 13 also presses against both the surface of the tooth 27 and down on the gum 19. Where the light contacts the lateral tooth surface 27, it causes it to transilluminate greatly in the area 21, causing a strong illumination 23 within the tooth cavity 29. When the light is adjusted away slightly from the lateral surface of the tooth 27, it causes a weaker transillumination 37 of the tooth 27, which provides a weaker illumination 39 within the tooth cavity 29. While I have illustrated and described the preferred embodiments of my invention, it is to be understood that these are capable of variation and modification, and I therefore do not wish to be limited to the precise details set forth, but desire to avail myself of such changes and alterations as fall within the purview of the following claims.

I claim:

1. Tooth transillumination apparatus for directing a relatively high intensity light beam directly against and through a side surface of a tooth to cause the tooth to transmilluminate and to give ample light within the tooth for accomplishing endodontic procedures, said tooth transillumination apparatus comprising, light source means for producing a relatively high intensity beam of light and having a light emitting end portion of relatively small size as compared to the side surface of a tooth so that said end portion can be located closely adjacent to the tooth to direct all of the light from said end portion into the side surface of the tooth, light source holder means for holding the light source means with said light emitting end portion closely adjacent to and in alignment with the side surface of the tooth to cause the tooth to be transilluminated by the relatively high intensity light emitted from said end of the light source means, and clamp means for clamping the light source holder means onto the tooth to be transilluminated and effective to retain said light emitting end portion of the light source means in alignment with the side surface of the tooth.

2. The invention defined in claim 1 wherein the light source means comprise an end of a fiber optic conduit.

* * * * *